(12) United States Patent
Struszczyk et al.

(10) Patent No.: US 7,482,019 B2
(45) Date of Patent: Jan. 27, 2009

(54) METHODS OF PRODUCING MODIFIED MICROCRYSTALLINE CHITOSAN AND USES THEREFOR

(75) Inventors: Henryk Struszczyk, Zgierz (PL); Antoni Niekraszewicz, Lodz (PL); Magdelena Kucharska, Lodz (PL); Alojzy Urbanowski, Lodz (PL); Maria Wisniewska-Wrona, Lodz (PL); Ewa Wesolowska, Lodz (PL); Danuta Ciechanska, Lodz (PL)

(73) Assignee: Abbott Laboratories, Abbott Park, IL (US)

( * ) Notice: Subject to any disclaimer, the term of this patent is extended or adjusted under 35 U.S.C. 154(b) by 304 days.

(21) Appl. No.: 10/501,202

(22) PCT Filed: Jan. 8, 2003

(86) PCT No.: PCT/IB03/00025

§ 371 (c)(1),
(2), (4) Date: Jul. 9, 2004

(87) PCT Pub. No.: WO03/057736

PCT Pub. Date: Jul. 17, 2003

(65) Prior Publication Data

US 2005/0019873 A1 Jan. 27, 2005

(30) Foreign Application Priority Data

Jan. 9, 2002 (PL) ...................................... 351600
Jan. 9, 2002 (PL) ...................................... 351601

(51) Int. Cl.
*A61K 9/00* (2006.01)
*A61K 36/06* (2006.01)

(52) U.S. Cl. .................. 424/400; 424/195.15; 424/484; 424/538

(58) Field of Classification Search ................. 424/400, 424/484, 538, 195.15
See application file for complete search history.

(56) References Cited

U.S. PATENT DOCUMENTS

| | | | |
|---|---|---|---|
| 4,833,237 A * | 5/1989 | Kawamura et al. ............ 536/20 |
| 4,970,150 A | 11/1990 | Yaku et al. |
| 5,554,445 A | 9/1996 | Struszczyk et al. |
| 5,720,793 A | 2/1998 | Kato et al. |
| 2007/0087415 A1 | 4/2007 | Struszczyk et al. |
| 2007/0087997 A1 | 4/2007 | Struszczyk et al. |
| 2007/0129326 A1 | 6/2007 | Struszczyk et al. |

FOREIGN PATENT DOCUMENTS

| | | | |
|---|---|---|---|
| FR | 2667072 A * | 3/1992 |
| FR | 2702144 | 9/1994 |
| JP | 63182304 | 7/1988 |
| JP | 64018530 | 1/1989 |
| JP | 01185301 | 7/1989 |
| JP | 02006950 | 1/1990 |
| JP | 02069502 | 3/1990 |
| JP | 06293801 | 10/1994 |
| JP | 9031104 | 2/1997 |
| JP | 02969431 | 11/1999 |
| PL | 160897 | 4/1993 |
| WO | WO 91/00298 | * 1/1991 |
| WO | 9109163 | 6/1991 |
| WO | WO 03/057736 | 7/2003 |

OTHER PUBLICATIONS

Piscitelli, et al., Chemical Abstracts Service., Accession #: 123:172489 (1993).
Piscittelli, et al., "Disposition of Phenylbutyrate and its Metabolites, Phenylacetate and Phenylacetylglutamine", *Oncology*, 35:368-373 (1995).
Patent Abstracts of Japan, #64-018530 (Jan. 23, 1989).
Patent Abstracts of Japan, #01-185301 (Jul. 24, 1989).
Patent Abstracts of Japan, #02-006950 (Jan. 11, 1990).
Patent Abstracts of Japan, #02-069502 (Mar. 8, 1990).
Patent Abstracts of Japan, #06-293801 (Oct. 21, 1994).
Patent Abstract JP 63182304, Derwent, 1988-252801/198836.
Patent Abstract JP 9031104A, Derwent, 1997-0161509/199715.
Database Chemabs 'Online! Chemical Abstracts Service, Columbus, Ohio, US; retrieved from STN Database accession No. 123:172489 XP002236421 abstract & PL 160 897 A (Instytut Wlokien Chemicznych) Apr. 30, 1993.
Database Chemabs 'Online! Chemical Abstracts Service, Columbus, Ohio, US; retrieved from STN Database accession No. 128:296087 XP002236422 abstract & Liu Yanru et al.: Fujian Shifan Daxue Xuebao, vol. 13, No. 3, 1997, pp. 67-70.
Database WPI Section Ch, Week 199951 Derwent Publications Ltd., London, GB; AN 1997-161509 XP002236424 & JP 02 969431 B (Kitosan Shokuhin Kogyo KK), Nov. 2, 1999 abstract.

* cited by examiner

*Primary Examiner*—Ruth A. Davis
(74) *Attorney, Agent, or Firm*—Workman Nydegger

(57) ABSTRACT

Disclosed are methods of producing modified microcrystalline chitosan. Chitosan in aqueous solution is degraded enzymatically, hydrolytically or oxidatively. The chitosan solution is then alkalized with agitation using aqueous hydroxides and/or their salts to attain a pH not lower than 7.0. The precipitated modified microcrystalline chitosan is highly pure and may be concentrated and dried according to known methods. Methods according to the invention also include methods by which an aqueous solution of chitosan is first alkalized using hydroxides and/or their salts to a pH not lower than 7.0. Then the precipitated microcrystalline chitosan is subjected to enzymatic or oxidative degradation to achieve a desired average molecular weight and polydispersity. The product is highly pure and may be concentrated and dried according to known methods.

8 Claims, No Drawings

METHODS OF PRODUCING MODIFIED MICROCRYSTALLINE CHITOSAN AND USES THEREFOR

FIELD OF THE INVENTION

The invention concerns a method to produce modified microcrystalline chitosan and uses thereof.

BACKGROUND OF THE INVENTION

Polish Patent No 125 995 and A Journal of Applied Polymer Science" vol. 33 p. 177, 1987 teach a method, to produce a chitosan with a developed internal surface in a batch process in which the chitosan is periodically precipitated from its solutions in aqueous organic or inorganic acids or their salts by means of hydroxides of alkali metals. The mixture is vigorously stirred. The precipitated chitosan in suspension form is washed with water several times. The well-known method produces chitosan with a developed internal surface with an out-put of 70-90% of theoretical values. The batch process requires at least 12-24 hours for a production cycle. The single batches of the product lack homogeneity. The product tends to degrade and its sorption capacity is rather poor, due to insufficient development of the inner surface. Polish Patent 164 247 and Finnish Patent FI 83 426 teach continuous methods to produce microcrystalline chitosan (MCCh). A solution of chitosan in aqueous acids and/or their salts is introduced to a reactor along with an aqueous hydroxide solution of alkali metals and/or their salts until microcrystalline chitosan is formed at pH>7. Simultaneously, the microcrystalline alkaline suspension of chitosan is continuously removed from the reactor. The alkaline solution may also be introduced directly to the recirculation system. Limitations of the process are: out-put below 90%, average agglomerate size above 1 μm and water retention value below 5000%.

Water retention value is an indication of the development of the inner surface. Another drawback of these processes is that it is not possible to control the molecular, and super molecular and morphological structure of the generated chitosan. The continuous process causes a substantial decrease of the average molecular weight of the generated MCCh as result of intensive degradation processes.

Polish Patent Application P 340 132 and the International Application WO 01/87 988 teach a method to produce modified microcrystalline chitosan. According to the disclosed process, a chitosan solution in aqueous solutions of acids and/or their salts with the polymer concentration not lower than 0.001 wt % is neutralized with aqueous hydroxides and/or their salts with a concentration in the range of 0.01-20% at intensive agitation with a rotary speed 10-1000 rpm to attain pH in the range 5.0-6.9; the chitosan salt is thereby converted into its gel form. The gel is homogenized at agitation speed in the range of 100-5000 rpm for not shorter than 10 seconds. Next, still with agitation 100-5000 rpm, the gel is alkalized with aqueous hydroxides in the concentration of 0.01-20 wt % to pH not lower than 6.9. The produced gel-like microcrystalline chitosan suspension is purified, possibly concentrated and dried according to known procedures. This method does not enable production of a modified microcrystalline chitosan with controlled molecular, super-molecular and morphological structure and assumed properties, particularly biological ones.

The invention also concerns a chitosan-calcium complex and a method to produce the complex. The sorption of metal ions by chitosan in its solid state or in aqueous organic and inorganic acid solutions in is well-known from following publications: journals-International Journal of Biological Macromolecules, v. 9, p. 109, 1987, "Carbohydrate Polymer", v. 8, p. 1-21, 1988, v. 11, p. 205-307, 1989; "Talanta", v. 16, p. 1571-1579, 1969; "Carbohydrate Polymers", v. 36, p. 267-276, 1998 and monographs "Chitin Chemistry", Mac Millan Press Ltd, Great Britain, 1992, p. 222-225 and "Advances in Chitin Science", v. IV, Universitat Potsdam, Germany, 2000, p. 202-205.

The amount of bound calcium (II) ions is insignificant compared to other alkali metals and amounts to only $0.4\text{-}0.8 \times 10^{-3}$ mol/gr of chitosan. Soluble derivatives of chitosan demonstrate a better ability to bind calcium II ions notably carboxymethylchitosan, carboxybenzylchitosan, (N)methylchitosan phosphoniate. Complexes of these derivatives with calcium II ions do not dissolve in water. Unknown are chitosan complexes with calcium (II) ions able to dissolve in water or to produce thermally stable suspensions.

SUMMARY OF THE INVENTION

The present invention addresses these and other issues.

Thus, according to one aspect, the present invention relates to methods for preparing modified microcrystalline chitosan by degrading chitosan in an aqueous acidic solution under conditions to achieve a desired molecular weight range and polydispersity. Then, the aqueous acidic solution is alkalized at vigorous agitation said acidic aqueous solution of chitosan with an aqueous base to form a solution having chitosan concentration of about 0.01-20 wt % and a pH of at least about 7.0. Microcrystalline chitosan can then be precipitated from this solution.

In another aspect, methods of the invention relate to techniques for preparing modified microcrystalline chitosan by first alkalizing at vigorous agitation an acidic aqueous solution of chitosan with an aqueous base to form a solution having chitosan concentration of about 0.01-20 wt % and a pH of at least about 7.0. The dissolved chitosan in this solution is then degraded under conditions to achieve a desired molecular weight range and polydispersity. The microcrystalline chitosan product can then be precipitated.

The present invention also relates to a chitosan-calcium (II) complex containing calcium (II) ions bound to microcrystalline chitosan prepared according to methods of the invention. These inventive complexes contain $\geq 0.01$ wt % chitosan having an average molecular weight $\geq 10$ kD, a polydispersity $\geq 2.0$, deacetylation degree $\geq 65\%$ and wherein said complex has a water retention value $\geq 300\%$, pH $\geq 7.1$ and a calcium (II) ion content $\geq 0.1$ wt % relative to chitosan.

In other aspects, the present invention also provides methods to produce a chitosan-calcium complex from a suspension of microcrystalline chitosan prepared according to methods of the invention. These suspensions can be mixed with $\geq 0.01$ wt % calcium (II) salt to form the inventive complexes of the invention.

DESCRIPTION OF THE INVENTION

Unlike in conventional techniques, methods for producing microcrystalline chitosan, according to the invention, precipitate the chitosan from its aqueous acidic solutions using aqueous hydroxides and/or their salts. According to these methods, chitosan with a concentration in aqueous solution of at least 0.001 wt % (preferably 0.1-2% wt %) is first degraded in a controlled way to attain an assumed average molecular weight and polydispersity degree. The chitosan under intensive agitation with rotary speed below 10,000 rpm is next alkalized with aqueous hydroxides and/or their salts with concentration in the range of 0.01-20 wt % to pH not lower than 7.0. The precipitated modified microcrystalline chitosan is purified and possibly concentrated and dried according to known methods.

The chitosan according to this invention is subjected to degradation by enzymatic, hydrolytic or oxidative treatment.

In enzymatic degradation, enzymes such as cellulases, chitanases or xylanases are used at a temperature not lower than 20° C., preferably 30-60° C. The degradation lasts 1 minute to 100 hours at enzyme activity not lower than 0.01 units/cm$^3$. The enzymes remaining after the treatment are deactivated at a temperature not lower than 70° C.

The hydrolytic degradation is run at a temperature not lower than 20° C., preferably 40-80° C., lasting 1 minute to 100 hours, preferably in the presence of strong acids such as hydrochloric acid or chloroacetic acid in an amount not lower than 0.001 wt % on chitosan.

The oxidative degradation according to the invention is conducted with oxidizing agents like hydrogen peroxide or sodium perborate in an amount not lower than 0.001 wt %, preferably 0.01-0.5% on chitosan, not shorter than 1 minute at a temperature not lower than 20° C., preferably 30-60° C. The method to produce modified microcrystalline chitosan, according to the invention consists also in that the chitosan, whose concentration in the aqueous acid solution is not lower than 0.001 wt %, preferably 0.1-2 wt % is intensely agitated with rotary speed not exceeding 10 000 rpm, alkalized to pH not lower than 7.0 with aqueous hydroxide solutions and/or their salts with 0.01-20 wt % concentration. The microcrystalline chitosan, precipitated from the solution, is next subjected to a controlled degradation to attain the assumed average molecular weight and polydispersity degree. The produced modified microcrystalline chitosan is purified and optionally concentrated and dried in a classical way.

Microcrystalline chitosan obtained, according to the invention, is subjected to either enzymatic or oxidative degradation. The enzymatic degradation of the microcrystalline chitosan uses enzymes active in neutral and/or alkaline media like cellulases at temperatures not lower than 20° C., preferably 30-60° C. for 1 minute to 100 hours at pH not lower than 7.0 with the enzymes activity not lower than 0.01 units/cm$^3$. The enzymes remaining after the degradation are deactivated at a temperature beyond 70° C. The oxidative degradation of the microcrystalline chitosan is conducted with the use of oxidizing agents like hydrogen peroxide or sodium perborate in the amount of at least 0.001 wt %, preferably 0.01-0.5 wt % on chitosan during not shorter than 1 minute at a temperature not lower than 20° C., preferably 30-60° C.

According to the invention, an aqueous solution of chitosan in acetic acid, lactic acid, citric acid or hydrochloric acid is used at pH not higher than 6.9. Aqueous solutions of sodium-, potassium- or ammonium hydroxide or/and the corresponding salts like sodium, potassium or ammonium carbonate are used during alkalization. The production of the microcrystalline chitosan, according to the invention can be run batchwise or continuously.

According to the invention, modified microcrystalline chitosan is produced with an assumed, controlled molecular, supermolecular and morphological structure following enzymatic, hydrolytic or oxidative degradation of the chitosan macromolecules, dissolved in aqueous acids in the course of the manufacture or the enzymatic or oxidative degradation of the microcrystalline chitosan precipitated from its solution. The enzymatic degradation enables production of microcrystalline chitosan with a relatively lower average molecular weight and polydispersity degree. In addition, the applied enzymes affect other properties of the microcrystalline chitosan like water retention value, size of molecules and crystallinity index. The hydrolytic degradation, particularly in the presence of strong acids, enables production of obtaining polymers with lowered average molecular weight and increased polydispersity. The modified microcrystalline chitosan, obtained according to the invention, is characterized by a wide spectrum of the average molecular weight compared to the initial chitosan.

The controlled degradation of chitosan in a homogeneous medium, prior to the manufacture of the microcrystalline chitosan, allows structural adaptation to the optimum conditions of the agglomeration. Thanks to the modification of the chitosan at this stage, the obtained microcrystalline chitosan is characterized by assumed physical-, chemical-, useful- and biological properties particularly bioactivity, biodegradability and biocompatibility. The degradation of the microcrystalline chitosan in the form of agglomerates according to the invention runs in a heterogeneous phase and enables a controlled modification of the chitosan structure, mainly the biodegradation of low molecular weight fractions, altering of morphological structure and widening the range of its properties like water retention value, porosity, sorption ability and biological activity. The degradation process, run this way, is simultaneously controlled by the diffusion of the enzymes or the oxidizing agent to the structure of the agglomerates. The assumed structure of the modified microcrystalline chitosan profoundly affects many of its properties like biodegradability, bioactivity, porosity, adhesion and miscibility with other polymers and stability. An advantage of the method of the invention is to produce modified microcrystalline chitosan with assumed properties in the forms of suspension, paste and powder according to the envisaged application.

Another essential advantage of the method according to the invention is the strict homogeneity and repeatability of the microcrystalline chitosan properties, a feature crucial for medical applications.

The modified microcrystalline chitosan obtained according to the invention is widely applied in medicine, veterinary and pharmacy.

The chitosan-calcium complex, according to the invention, constitutes a compound of calcium (II) ions and microcrystalline chitosan and contains not less than 0.01% of the polymer with an average molecular weight $M_V$ not less than 10 kD, a polydispersity degree ($P_d$) not lower than 2.0 and a deacetylation degree (DD) not less than 65%. The complex is characterized by a water retention value WRV not lower than 300%, a pH not lower than 7.0 and calcium Ca (II) ions' content not lower than 0.1 wt % on chitosan.

According to the invention, the Ca (II) ions are linked with the microcrystalline chitosan (MCCh) by coordinate and/or second-order bonds like hydrogen bonds. The method to produce the chitosan-calcium complex, according to the invention, is carried out as follows: to a MCCh suspension containing not less than 0.01 wt % of the polymer with a $M_V$ not less than 10 kD, a $P_d$ not lower than 2.0, a DD not lower than 65%, a WRV not lower than 300% and pH not lower than 7.0, calcium salts like calcium chloride or calcium acetate are added in the amount of not less than 0.1 wt % Ca (II), preferably 10-50 wt % on chitosan. The mixture is next homogenized and reacted at a temperature not lower than 10° C., preferably 20-40° C. for at least 1 minute, preferably 302-120 minutes. The produced chitosan-calcium is possibly condensed and dried, according to known methods.

The production of the chitosan-calcium complex may be accomplished in two steps: in the first step the mixture of MCCh and calcium salt is homogenized at an agitation speed not exceeding 100 rpm, in the second step the chitosan-calcium complex is formed at 100-5000 rpm.

The chitosan-calcium complex is characterized by the presence of mainly coordinate bonds between the calcium ions and the amide- and hydroxide groups of the chitosan and by the forming the intra- and intermolecular hydrogen bonds between amide-, amino- and hydroxide groups of the chitosan chain. These bonds are characterized by high bond energy. The presence of the bonds makes the structure of the chitosan-calcium complex durable resulting in an excellent stability of the complex with high content of calcium ions.

The advantage of methods according to the invention, is a simple procedure to produce the chitosan-calcium complex, characterized by unique properties like high content bound calcium (II) ions, high water retention value, good stability even at elevated temperatures and a high biological activity compared to known forms of chitosan.

The chitosan complex finds its application mainly in medicine and pharmacy.

The method according to the invention is illustrated with following examples, which do not limit its range of application.

EXAMPLE 1

To a reactor equipped with an agitator and cooling/heating jacket 1500 wt parts of a 0.5% aqueous chitosan solution in a 0.25% aqueous solution of lactic acid were introduced. The polymer was characterized by an average molecular weight $M_V$=345.6 kD a deacetylation degree DD=82.2% and a polydispersity $P_d$=3.45. Next, to the reactor, with the agitator on at the speed of 150 rpm, a 10% aqueous sodium hydroxide was introduced with the rate of 50 cm$^3$/min to attain pH=5.5, then 1.5 wt parts of a solution of the Ekonaza CE cellulase were introduced. The initial endo-1,4-β-glucanase activity of the enzymes solution was 2600 U CMC/cm$^3$.

The activity of the cellulase in the reacting mixture was 2.6 U CMC/cm$^3$. The enzymatic degradation run at the temperature of 20° C. for 16 hours at continuous agitation. After that time the enzymes were deactivated at 80° C. for 15 minutes.

The reactor content was next cooled to 25° C. and, with continuous agitation at 150 rpm, a 1% aqueous solution of sodium hydroxide was introduced during 30 minutes to pH=8.0 and precipitation of the agglomerates of the modified microcrystalline chitosan (MCCh). Under these conditions the reactor content was homogenized for further 15 minutes. The chitosan product was purified by continuous washing with water to pH=7.25 and complete removal of impurities.

The product was next concentrated. 280 wt parts of a modified MCCh were obtained in the form of a white gel-like suspension with a concentration of 2.41 wt % of the polymer characterized by $M_V$=60.1 kD, $P_d$=2.09, DD=82.2%, and water retention value WRV=1630%.

EXAMPLE 2

To the reactor, as in Example 1, 1500 wt parts of a 0.5% aqueous chitosan solution in a 0.25% aqueous solution of lactic acid were introduced. The polymer was characterized by: $M_V$=237.0 kD, DD=84.3%, $P_d$=3.49. Next to the reactor with the agitator on at speed of 150 rpm a 1% aqueous solution of sodium hydroxide was introduced at a rate of 25 cm$^3$/min to attain pH=5.2.

Next, 1.5 wt parts of Ekonaza CE cellulase solution were introduced. The initial endo-1,4-β-glucanase) activity of the enzyme solution amounted to 2600 U CMC/cm$^3$. The enzyme activity in the reaction mixture was 2.6 U CMC/cm$^3$. The enzymatic degradation was conducted at 20° C. for 1 hour. Afterwards, the enzymes were deactivated at 80° C. for 5 minutes. The reactor content was next cooled to 21° C. and, at continuous agitation with 150 rpm, a 5.0% aqueous ammonia solution was introduced during 30 minutes to attain pH=8.0 and to precipitate agglomerates of the modified MCCh. Under these conditions the reactor content was homogenized for a further 30 minutes.

The resulting MCCh was purified by continuous washing with water to pH=7.2 and complete removal of impurities. Next the MCCh was concentrated.

210 wt parts of modified MCCh were obtained in the form of a white gel-like suspension with a 3.25 wt % concentration of the polymer characterized by: $M_V$=209.9 kD, $P_d$=3.16, DD=84.2%, WRV=955.0%.

EXAMPLE 3

To the reactor as in Example 1, 20000 wt parts of a 1.0% aqueous solution of chitosan in a 0.4% aqueous hydrochloric acid solution were introduced. The polymer was characterized by: $M_V$=796.5 kD, DD=85.6%, $P_d$=3.23. Next, to the reactor, with the agitator on at 480 rpm, a 0.5% aqueous solution of sodium hydroxide was added with the rate of 50 cm$^3$/min to attain pH=5.2. 11 wt parts of the cellulase Ekonaza CE solution were added. The 1,4-β-glucanase activity of the initial enzyme was 2600 U CMC/cm$^3$, whereas in the reaction mixture it was 1.315 U CMC/cm$^3$. The controlled enzymatic degradation was run at 20° C. for 15 minutes followed by deactivation of the enzymes at 80° C. for 15 minutes.

Next, the reactor content was cooled to 25° C. and, with the agitator on at 480 rpm, a 0.5% aqueous sodium hydroxide was introduced during 90 minutes to attain pH=7.69 and precipitate agglomerates of the modified MCCh. Under these conditions the reactor content was homogenized for further a 15 minutes. The product MCCh was purified by washing with water to pH=7.3 and complete removal of impurities. 5015 wt parts of the modified MCCh were obtained as a white, gel-like suspension with the polymer concentration of 3.46 wt %. The polymer was characterized by $M_V$=387.0 kD, $P_d$=3.13, DD=85.6% and WRV=870.0%.

EXAMPLE 4

To the reactor as in Example 1, 1000 wt parts of a 1.0% aqueous solution of chitosan in a 0.4% aqueous solution of hydrochloric acid were introduced. The polymer was characterized by: $M_V$=796.5 kD, DD=85.6%, $P_d$=3.23. Next, to the reactor with the agitator on at 1000 rpm, a 0.75% aqueous solution of sodium hydroxide was introduced at the rate of 50 cm$^3$/min to attain pH=6.53. 0.2 wt part of the Ekonaza CE cellulase was added. The initial endo-1,4-β-glucanase activity of the enzyme was 2600 U CMC/cm$^3$ and the activity in the mixture was 0.52 U CMC/cm$^3$. The controlled enzymatic degradation was run at 20° C. for 10 min, then the enzymes were deactivated at 80° C. for 10 minutes. The reactor content was next cooled to 25° C. and, at continuous agitation with 4000-4500 rpm, a 0.75% aqueous sodium hydroxide was introduced during 30 minutes to attain pH=7.65 and precipitate the modified MCCh. Under these conditions the reactor content was homogenized for further 15 minutes. The obtained MCCh was purified by continuous washing with water to pH=7.15 and complete removal of impurities. The product was next concentrated.

415 wt parts of modified MCCh were obtained as a white gel-like suspension with the polymer concentration of 2.12 wt % characterized by: $M_V$=514.0 kD, $P_d$=2.90, DD=85.6% and WRV=1100.0%.

EXAMPLE 5

To the reactor as in Example 1, 1500 wt parts of a 0.75% chitosan solution with properties as in Example 2 in a 0.5% aqueous solution of lactic acid were introduced. Next, to the reactor with continuous agitation at 1000 rpm, a 2% aqueous sodium hydroxide at the rate of 50 cm$^3$/minute was introduced to attain pH=6.0 and 3.9 wt parts of xylanase were added with the initial endo-1,4-β-xylanase activity of 13949 U xyl/cm$^3$ and endo-1,4-β-glucanase activity of 411 U CMC/cm$^3$. The enzyme activity in the reaction mixture was 37 U xyl/cm$^3$ and 1.1 U CMC/cm$^3$ respectively. The controlled enzymatic degradation was conducted at 20° C. for 15 minutes followed by a deactivation of the enzyme at 80° C. for a further 15 minutes. Next, the reaction mixture was cooled to 20° C. and, with continuous 1000 rpm agitation, a 2.0% aqueous sodium hydroxide was introduced during 30 minutes to attain pH=6.80.

Then, the agitation speed was increased to 8000 rpm and the agglomeration process was run for 15 minutes to attain pH=7.50 and precipitate the agglomerates of the modified MCCh. Under these conditions, the reactor content was homogenized for a further 15 minutes. The obtained modified MCCh was purified by a continuous washing with water to attain pH=7.2 and complete removal of impurities. 320 wt parts were obtained of the modified MCCh as a white gel-like suspension with a 3.18% concentration of the polymer characterized by $M_V$=140.0 kD, $P_d$=3.04, DD=84.3%, WRV=3800%.

EXAMPLE 6

To the reactor, as in Example 1, 2000 wt parts of a 0.25% aqueous chitosan solution in 0.6% aqueous solution of acetic acid were introduced. The polymer was characterized by: $M_V$=143.9 kD, DD=78.5% and $P_d$=2.94. Next, to the reactor with the agitator at 200 rpm, a 5% aqueous solution of sodium hydroxide was introduced to attain pH=6.80, next 20 wt parts were added of a neutral cellulase with the initial endo-1,4-β-glucanase activity of 186 U CMC/cm$^3$. The enzyme activity in reaction mixture was 1.9 U CMC/cm$^3$. The controlled enzymatic degradation was conducted at 20° C. for 5 hours followed by deactivation of the enzyme at 80° C. for a further 15 minutes.

The reaction mixture was next cooled to 18° C. With continuous agitation at 200 rpm, a 5.0% aqueous sodium hydroxide was introduced during 60 minutes to attain pH=8.0 and precipitate the agglomerates of the modified MCCh. Under these conditions, the reactor content was homogenized for a further 15 minutes. The obtained, modified MCCh was purified by a continuous washing with water to attain pH=7.2-7.3 and complete removal of impurities. The product was next concentrated.

150 wt parts of a modified MCCh were obtained as a grey gel-like suspension with a concentration of the polymer of 2.99 wt %. The polymer was characterized by $M_V$=44.3 kD $P_d$=3.25, DD=78.5%, and WRV=1250%.

EXAMPLE 7

To a reactor equipped as in Example 1, 1500 wt parts of a 0.5% chitosan solution in a 0.25% aqueous hydrochloric acid were introduced. The polymer was characterized by: $M_V$=345.6 kD, DD=82.2%, $P_d$=2.92. Next to the reactor with continuous agitation at 150 rpm a 5.0% aqueous sodium hydroxide was added at the rate of 125 cm$^3$/min to attain pH=7.9 and precipitate the agglomerates of MCCh. Under these conditions, homogenization was continued for a further 15 minutes.

Next, to the reactor 15.4 wt parts of a neutral cellulase were introduced with the initial activity of endo-1,4-β-glucanase- 186 U CMC/cm$^3$. The enzymatic activity in the reaction mixture was 1.9 U CMC/cm$^3$. The controlled enzymatic degradation was conducted at 20° C. during 2 hours with continuous agitation. The enzyme was, afterwards, deactivated for 5 minutes at 80° C. Next the reaction mixture was cooled to 20° C. and at continuous 200 rpm agitation a 5.0% aqueous sodium hydroxide was introduced during 60 minutes to attain pH=7.8 and precipitate agglomerates of the modified MCCh. Under these conditions homogenization was continued for a further 15 minutes. The modified MCCh was purified by continuous washing with water to pH=7.2-7.3 and complete removal of water.

250 wt parts of modified MCCh were obtained, as a grey gel-like suspension containing 2.64 wt % of the polymer characterized by $M_V$=167.6 kD, $P_d$=2.77, DD=62.6%, WRV=1860%.

EXAMPLE 8

To a reactor equipped with agitator, heating jacket and a recirculation assembly with an impeller pump 1000 wt parts of a 1% chitosan solution in a 4.0% aqueous acetic acid were introduced. The polymer was characterized by $M_V$=734 kD, $P_d$=3.54 and DD=73.8%. With the agitator at 800 rpm and the recirculation assembly switched on 1.5 wt parts of an aqueous solution of the cellulase Ekonaza CE were introduced to the chitosan solution at pH=4.5. The initial endo-1,4-β-glucanase activity of the enzyme was 2600 U CMC/cm$^3$, while in the reaction mixture it was 2.6 U CMC/cm$^3$. The controlled enzymatic degradation was conducted for 30 minutes at 30° C. Next, a 4.0% aqueous solution of a mixture of potassium hydroxide and potassium carbonate in the weight proportion 1:1 were introduced to the reactor till the precipitation of the modified MCCh agglomerates at pH=7.8.

Afterwards, a 1% aqueous chitosan solution in 4.0% aqueous acetic acid at a rate of 1200 wt parts/hour and a 4.0% aqueous solution of a mixture of potassium hydroxide and potassium carbonate at a rate of 869 wt parts/hour were introduced to the reactor to pH=7.9±0.3. Simultaneously, an aqueous solution of a cellulase derived from *Humicola insoleus mycelium* was continuously fed to the reactor. The enzyme endo-1,4-β-glucanase was 0.75 U CMC/cm$^3$. A suspension of the modified MCCh was continuously removed from the reactor at a rate adequate to keep the reaction volume in the reactor constant. Next, the suspension was passed through a heat exchanger to deactivate the remaining enzyme at 85° C., cooled to 25° C. and directed to an intermediate tank. From the tank the modified MCCh suspension was continuously fed to an ultrafiltration unit equipped with a rolled membrane with 40 kD cut-off.

Modified MCCh as a stable, white colored suspension was obtained with following properties: polymer content— 0.45%, $M_V$=480 kD, $P_d$=3.22, DD=73.8%, WRV=1350%, pH=7.25. The output of the product was 28.5 wt parts of MCCh from 1000 volume units of the reactor per hour.

EXAMPLE 9

1500 wt parts of a 1.5% chitosan solution in a 2% aqueous acetic acid were introduced to a reactor as in Example 1. The chitosan was characterized by $M_V$=345.0 kD, DD=82.2%, $P_d$=3.47. Next 500 wt parts of a 1.5% aqueous hydrochloric acid were introduced to the reactor and the controlled hydrolytic degradation was accomplished for 1 hour at 40° C. and 600 rpm of the agitator. Then a 2.5% aqueous sodium hydroxide was continuously added to the reaction mixture at a rate of 25 cm³/min and 1500 rpm of the agitator to attain pH=7.7 and precipitate the agglomerates of the MCCh. The agitation was continued for a further 0.5 hour at 4000 rpm. The obtained product was purified by ultrafiltration with a rolled membrane (cut-off=40 kD) to attain pH=7.15 and a complete removal of impurities.

680 wt parts of modified MCCh were obtained as a white gel-like suspension with 3.2% concentration of the polymer characterized by $M_v$=220 kD), $P_d$=381, DD=82.2%, WRV=1750%.

EXAMPLE 10

1000 wt parts of a 1.0% chitosan solution in a 4.0% aqueous acetic acid were introduced to the reactor as in Example 1. The chitosan was characterized by $M_V$=345.0 kD, DD=82.2%, $P_d$=3.47.

Next, the controlled hydrolytic degradation was run for 5 hour at 60° C. with 600 rpm of the agitator. Next, a 2.5% aqueous sodium hydroxide was added at the rate of 50 cm³/min with 1500 rpm of the agitator to precipitate the agglomerates of MCCh and attain pH=7.7. The agitation was continued for a further 0.5 hour at 4000 rpm. The obtained product was purified by ultrafiltration with a rolled, 40 kD cut-off membrane to attain pH=7.15 and complete removal of impurities.

360 wt parts of the modified MCCh were obtained as a white gel-like suspension with a 2.5% content of the polymer characterized by $M_v$=250 kD, $P_d$=3.67, DD=82.2%, WRV=1450%.

EXAMPLE 11

1000 wt parts of a 1.0% chitosan solution in a 1.0% aqueous hydrochloric acid were introduced to the reactor as in Example 1. The polymer was characterized by $M_V$=345.0 kD, DD=82.2%, $P_d$=3.47. Next, the controlled hydrolytic degradation was run for 3 hours at 50° C. and 600 rpm of the agitator. Afterwards, a 2.5% aqueous sodium hydroxide was continuously added at a rate of 50 cm³/min and 1500 rpm of the agitator to attain pH=7.8 and precipitate the agglomerates of MCCh. The agitation was continued for a further 0.5 hour at 4000 rpm. The obtained product was purified by ultrafiltration using a rolled membrane with a 40 kD cut-off to attain pH=7.2 and a complete removal of impurities.

320 wt parts of the modified MCCh were obtained as a white, gel-like suspension with a 2.8% content of the polymer, characterized by $M_V$=200 kD, $P_d$=3.98, DD=82.2%, WRV=1200%.

EXAMPLE 12

1000 wt parts of a 1.0% chitosan solution in a 2.0% aqueous acetic acid were introduced to the reactor as in Example 1. The polymer was characterized by $M_V$=345.0 kD, DD=82.2% and $P_d$=3.47. Next, the oxidative controlled degradation was conducted in the presence of 35 wt parts of a 10% hydrogen peroxide solution during 2 hours at 30° C. with 600 rpm of the agitator.

Then, to the reaction mixture a 1.5% aqueous sodium hydroxide was introduced with a rate of 50 cm³/min and 1500 rpm of the agitator to attain pH=7.8 and precipitate the agglomerates of the MCCh. The agitation was continued for a further 0.5 hour at 3500 rpm. The obtained product was purified by ultrafiltration using a rolled membrane with a 40 kD cut-off to attain pH=7.15 and complete removal of impurities.

325 wt parts of the modified MCCh were obtained as a white, gel-like suspension with a 2.8 wt % content of the polymer characterized by $M_v$=220 kD, $P_d$=3.62, DD=82.2% and WRV=1300%.

EXAMPLE 13

1000 wt parts of a 1.0% chitosan solution in a 0.4% aqueous hydrochloric acid were introduced to the reactor as in Example 1. The polymer was characterized by: $M_V$=345.0 kD, DD=82.2 and $P_d$=347. Next, the oxidative controlled degradation was conducted in the presence of 40 wt parts of a 1.0% hydrogen peroxide solution during 3 hours at 20° C. with 500 rpm of the agitator. Then, a 0.75% aqueous sodium hydroxide was continuously introduced at the rate of 50 cm³/min and 1500 rpm of the agitator. Agitation was continued for a further 0.5 hour at 4000 rpm. The obtained product was purified by ultrafiltration with a rolled membrane with 40 kD cut-off to attain pH=7.22 and a complete removal of impurities.

220 wt parts of a modified MCCh were obtained as a white, gel-like suspension with a 2.5% content of the polymer, characterized by: $M_V$=120 kD, $P_d$=3.78, DD=82.2% and WRV=1500%.

The following examples illustrate use of modified microcrystalline chitosan according to the invention to prepare chitosan-calcium complexes.

EXAMPLE 14

100 wt parts of a gel-like suspension of microcrystalline chitosan (MCCh) characterized by a polymer content of 2.5 wt %, an average polymerization degree $M_V$=250 kD, a polydispersity $P_d$=2.48, a water retention value WRV=1240%, deacetylation degree DD=83.2% and a pH=7.2, were introduced to a mixer equipped with a slow/fast agitating system. Then, for 15 minutes, 2.5 wt parts of calcium chloride with the granulation of 100 mesh. were added at continuous agitation with 150 rpm. During 10 minutes the mixture was homogenized at 23° C. and next, during 10 minutes, the chitosan-calcium complex was formed at agitation speed of 4500 rpm. 102.5 wt parts of a stable suspension of the chitosan-calcium complex were obtained, containing 2.46 wt % of polymer characterized by $M_v$=245 kD, $P_d$=2.56, DD=83.2%, WRV=850%, pH=7.11 and 21.98 wt % content of calcium Ca (II), on weight of chitosan.

EXAMPLE 15

120 wt parts of a modified microcrystalline chitosan in the form of a gel-like suspension, characterized by 3.2 wt % content of the polymer with $M_v$=602 kD, $P_d$=2.96, DD=85.6%, WRV=750% and pH=7.24, were introduced to a mixer as in Example 1. Then, for 5 minutes, 1.0 wt part of calcium chloride with the granulation of 100 mesh was added at a constant agitation with 150 rpm. The forming of the chitosan-calcium complex was accomplished in two steps: first at 26° C. with an agitation of 100 rpm for 15 minutes and second with 4000 rpm for 45 minutes.

121 wt parts of a stable suspension of the chitosan-calcium complex were obtained containing 2.97 wt % of polymer, characterized by $M_v$=590 kD, $P_d$=2.96, DD=85.6%, WRV=650%, pH=7.15 and a 5.73 wt % content of calcium Ca (II), on weight of chitosan.

EXAMPLE 16

150 parts of a modified microcrystalline chitosan, characterized by a polymer content of 2.5 wt %, $M_v$=602 kD, $P_d$=2.96, DD=85.6%, WRV=750% and pH=7.24, were introduced to the mixer as in Example 1. Next, with a constant agitation at 150 rpm 1.8 wt parts of calcium chloride with the granulation of 80 mesh, were introduced during 5 minutes. The process of forming the chitosan-calcium complex was conducted at 30° C. during 60 minutes. 151.8 wt parts of the chitosan-calcium complex were obtained as a stable chitosan suspension of its microcrystalline form, containing 2.47% of the polymer, characterized by $M_v$=590 kD, $P_d$=3.06, DD=85.6%, WRV=710%, pH=7.14 and 10.56 wt % content of calcium Ca (II), on weight of chitosan.

EXAMPLE 17

100 wt parts of microcrystalline chitosan in a gel-like suspension characterized by a polymer content of 2.85 wt % with $M_v$=590 kD, $P_d$=3.58, WRV=980 and pH=7.3 were introduced to the mixer as in Example 1. Next, 100 wt parts of a 10% aqueous solution of calcium acetate were added. The content of the mixer was homogenized and reacted for 1 hour at 15° C. Then, the obtained suspension of the chitosan-calcium complex was condensated by filtration.

120 wt parts of the chitosan-calcium complex were obtained as a stable suspension, containing 2.43 wt % of polymer characterized by $M_v$=582 kD, $P_d$=3.52, WRV=700%, pH=7.25 and a calcium Ca (II) content of 4.9%, on weight of chitosan.

We claim:

1. A method for preparing modified microcrystalline chitosan, comprising the steps of:
   firstly, dissolving chitosan into an aqueous acidic solution;
   second, degrading chitosan in an aqueous acidic solution under conditions to achieve a desired molecular weight range and polydispersity, said solution having a concentration of at least about 0.001 wt % of chitosan, wherein the degrading is enzymatic, hydrolytic, or oxidative, said degrading comprising at least one of the following:
   introducing at least one of cellulases, chitanases, or xylanases with an enzymatic activity greater than 0.01 units/cm$^3$ into the aqueous acidic solution at a temperature between 30 degrees C. and 60 degrees C. for up to 100 hours, and then increasing the temperature to above 70 degrees C. to deactivate the enzyme;
   incubating the chitosan in the acidic solution having chydrochloric acid or chloroacetic acid at an amount greater than 0.001 wt % of the chitosan at a temperature between 40 degrees C. and 80 degrees C. for up to 100 hours; or
   introducing an oxidative agent into the acidic solution at a temperature greater than 30 degrees C. to 60 degrees C., wherein the oxidative agent is 10% hydrogen peroxide or sodium perborate in an amount between 0.01 wt % to 0.5 wt % of the chitosan;
   thirdly, alkalizing at vigorous agitation said acidic aqueous solution of chitosan with an aqueous base to form an alkaline solution having chitosan concentration of about 0.01-20 wt %, said alkaline solution having a pH greater than 7.0, wherein the base is a hydroxide or ammonia; and
   fourthly, precipitating said microcrystalline chitosan from said alkaline solution.

2. A method according to claim 1, wherein the degrading is enzymatic.

3. A method according to claim 1, wherein the degrading is hydrolytic.

4. A method according to claim 1, wherein the degrading is oxidative.

5. A method according to claim 1, wherein said chitosan has a concentration in said aqueous acidic solution is between 0.1 to 2 wt %.

6. A method according to claim 1, wherein said alkalizing step uses a base selected from the group consisting of sodium hydroxide, potassium hydroxide and ammonium hydroxide.

7. A method according to claim 1, wherein said alkalizing step uses a base selected from the group consisting of sodium carbonate, potassium carbonate and ammonium carbonate.

8. A method according to claim 1, wherein said aqueous acidic solution of chitosan comprises an acid selected from the group consisting of acetic acid, lactic acid, citric acid and hydrochloric acid, said acidic solution having a pH of ≦6.9.

* * * * *

UNITED STATES PATENT AND TRADEMARK OFFICE
CERTIFICATE OF CORRECTION

PATENT NO. : 7,482,019 B2  Page 1 of 1
APPLICATION NO. : 10/501202
DATED : January 27, 2009
INVENTOR(S) : Struszczyk et al.

It is certified that error appears in the above-identified patent and that said Letters Patent is hereby corrected as shown below:

Column 2
Line 1, delete "in"

Column 5
Line 61, change "at speed" to --at a speed--
Line 65, delete ")"

Column 6
Line 38, change "further a" to --a further--

Column 9
Line 22, delete ")"
Line 32, change "hour" to --hours--

Column 10
Line 51, change "mesh." to --mesh--

Signed and Sealed this

Sixteenth Day of March, 2010

David J. Kappos
*Director of the United States Patent and Trademark Office*